(12) United States Patent
Meltzer et al.

(10) Patent No.: US 8,735,397 B2
(45) Date of Patent: May 27, 2014

(54) METHOD FOR TREATING SCHIZOPHRENIA AND RELATED DISEASES

(75) Inventors: Herbert Y. Meltzer, Nashville, TN (US); Masakuni Horiguchi, Nashville, TN (US)

(73) Assignees: Vanderbilt University, Nashville, TN (US); Dainippon Sumitomo Pharma Co., Ltd., Osaka (JP)

( * ) Notice: Subject to any disclaimer, the term of this patent is extended or adjusted under 35 U.S.C. 154(b) by 263 days.

(21) Appl. No.: 13/072,996

(22) Filed: Mar. 28, 2011

(65) Prior Publication Data

US 2011/0237602 A1    Sep. 29, 2011

Related U.S. Application Data

(60) Provisional application No. 61/318,534, filed on Mar. 29, 2010.

(51) Int. Cl.
| | | |
|---|---|---|
| *A61K 31/497* | (2006.01) | |
| *A61K 31/525* | (2006.01) | |
| *A61K 31/50* | (2006.01) | |
| *C07D 241/04* | (2006.01) | |

(52) U.S. Cl.
USPC ............... 514/252.13; 514/245.04; 544/358

(58) Field of Classification Search
USPC .................................................. 514/252.13
See application file for complete search history.

(56) References Cited

U.S. PATENT DOCUMENTS

| | | |
|---|---|---|
| 5,532,372 A | 7/1996 | Saji et al. |
| 5,688,826 A | 11/1997 | Massey et al. |
| 5,780,632 A | 7/1998 | Saji et al. |
| 6,964,962 B2 | 11/2005 | Wong et al. |
| 2002/0156067 A1 | 10/2002 | Wong et al. |
| 2006/0003992 A1 | 1/2006 | Wong et al. |
| 2008/0312286 A1 | 12/2008 | Pinkerton et al. |
| 2011/0190345 A1 | 8/2011 | Huszar et al. |

FOREIGN PATENT DOCUMENTS

| | | |
|---|---|---|
| JP | 05-017440 A | 1/1993 |
| WO | 97/18199 A1 | 5/1997 |
| WO | 98/32436 A1 | 7/1998 |
| WO | 02/053140 A2 | 7/2002 |
| WO | 03/066039 A1 | 8/2003 |
| WO | 2006/015158 A1 | 2/2006 |
| WO | 2009/020569 A1 | 2/2009 |
| WO | 2010/060742 A1 | 6/2010 |

OTHER PUBLICATIONS

Meyer et al. (Lurasidone: a new drug in development for schizophrenia. Expert Opin Investig Drugs. Nov. 2009;18(11):1715-26).*
Patil et al. (Activation of mGlu2/3 receptors as a new approach to treat schizophrenia: a randomized Phase 2 clinical trial. Nature Medicine 13, 1102-1107 (2007)).*
Extended European Search Report dated May 14, 2013, issued against corresponding European Application 11762917.0.
Mark E. Fraley, "Positice allosteric modulators of the metabotropic glutamate receptor 2 for the treatment of schizophrenia", Expert Opinion on Therapeutic Patents, Informa Healthcare, GB, vol. 19, No. 9, (2009) pp. 1259-1276.
Marek et al., "Metabotropic glutamate2/3 (mGlu2/3) receptors, schizophrenia and cognition", European Journal of Pharmacology, Elsevier Science, vol. 639, No. 1-3, Aug. 10, 2010, pp. 81-90.
Meyer, J.M. et al., "Lurasidone: a new drug in development for schizophrenia", Expert Opinion, Investig. Drugs (2009) 18(11), pp. 1715-1726.
Conn, P.J. et al., Neuropsychopharmacology Reviews, (2009), 34: pp. 248-249.
Snigdha, S. et al., "Attenuation of Phencyclidine-Induced Object Recognition Deficits by the Combination of Atypical Antipsychotic Drugs and Pimavanserin (ACP 103), a 5-Hydroxyttyptamine . . . ", The Journal of Pharmacology and Experimental Therapeutics, vol. 332, No. 2, (2010), pp. 622-631.
Gonzalez-Maeso, J. et al., "Idenfitication of a serotonin/glutamate receptor complex implicated in psychosis", Nature, vol. 452, Mar. 6, 2008, pp. 93-97.
International Preliminary Report on Patentability dated Oct. 2, 2012, issued in PCT/JP2011/058493.
International Search Report dated Jul. 12, 2011, issued in International Application No. PCT/JP2011/058493.

* cited by examiner

*Primary Examiner* — Layla Soroush
(74) *Attorney, Agent, or Firm* — Fitch, Even, Tabin & Flannery LLP

(57) ABSTRACT

The invention relates to a method for treating schizophrenia and/or related diseases comprising administering lurasidone and a mGluR2 ligand to a mammal in need thereof.

11 Claims, 6 Drawing Sheets

Lurasidone dose response curve; sub-effective dose is 0.03mg/kg, effective dose is 0.1mg/kg.

Co-administration of LY379268 with sub-effective dose of Clozapine significantly reversed the PCP-induced deficit.

METHOD FOR TREATING SCHIZOPHRENIA AND RELATED DISEASES

CROSS REFERENCE TO RELATED APPLICATION

This application is a utility application and claims the benefit of U.S. Provisional Application No. 61/318,534, filed Mar. 29, 2010 the complete disclosure of which is incorporated herein by reference.

TECHNICAL FIELD

The invention relates to a method for treating schizophrenia and/or related diseases comprising administering two or more ingredients, and a pharmaceutical product thereof. In more detail, the instant invention is directed to a method for treating schizophrenia and/or bipolar disorder which comprises administering lurasidone and a mGluR2 ligand to a mammal in need thereof, and other invention categories thereof.

BACKGROUND ART

Lurasidone [chemical name: (3aR,4S,7R,7aS)-2-{(1R,2R)-2-[4-(1,2-benzisothiazol-3-yl)piperazin-1-ylmethyl]cyclo-hexylmethyl}hexahydro-4,7-methano-2H-isoindole-1,3-dione] of the following formula is a novel psychotropic agent, which is characteristic of a high affinity for dopamine $D_2$, serotonin 5-$HT_{1A}$, 5-$HT_{2A}$, 5-$HT_7$, and noradrenaline $\alpha_{2C}$ receptors and of minimal to no affinity for histamine $H_1$ and muscarinic $M_1$ receptors. Lurasidone possesses antipsychotic effects, antidepressant- or anxiolytic-like effects, and pro-cognitive effects with potentially reduced liability for extrapyramidal and CNS depressant side effects, which is expected to be used for the treatment of schizophrenia and bipolar disorder (Japan Patent Application JP-5(1993)-17440 A; J M Meyer et al. *Exp Opin Invest Drugs* 18(11): 1715-1726 (2009)).

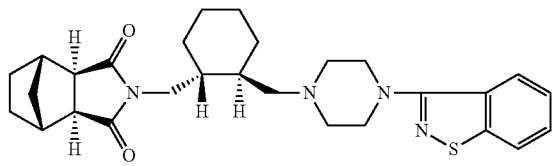 [SMILES: O=C1[C@@H]2[C@H]3CC[C@H](C3)[C@@H]2C(=O)N1C[C@@H]1CCCC[C@H]1CN1CCN(c2nsc3ccccc23)CC1]

Metabotropic glutamate receptors (mGluRs) are subclassified into three groups, the group I mGluRs (mGluR1 and mGluR5), the group II mGluRs (mGluR2 and mGluR3) and the group III mGluRs (mGluR4, mGluR6, mGluR7 and mGluR8). The group II mGluRs, mGluR2 and mGluR3, have emerged as exciting and well-validated targets for novel therapeutic agents used for treating psychiatric disorders (J P Conn et al., *Neuropsychopharmacol Rev* 34: 248-249 (2009)). A large number of preclinical and clinical studies provide strong evidence that mGluR2/3 agonists may provide a novel approach to the treatment of anxiety disorders and schizophrenia. Recently, a novel class of compounds, known as mGluR2 positive allosteric modulaters (PAMs), has shown the efficacies in the animal models that are related with the prediction of both antipsychotic and anxiolytic activities, that are very similar to those observed with mGluR2/3 agonists. While the mGluR2/3 agonists bind to orthosteric binding site of endogenous ligand glutamate, mGluR2 PAMs bind to a site distinct from the glutamate binding site to increase the responses of mGluR2 to glutamate without activating mGluR2 directly.

DISCLOSURE OF INVENTION

The present inventors have extensively studied to find out more potent psychotropic agents and then have found that the novel combination of the present invention exhibit the desired pharmacological actions. Based upon the new findings, the present invention has been completed.

In one embodiment, the instant invention is directed to a method for treating schizophrenia and/or bipolar disorder which comprises administering a therapeutically effective amount of lurasidone or a pharmaceutically acceptable acid addition salt thereof, and a therapeutically effective amount of a mGluR2 ligand to a mammal in need thereof.

In one embodiment, the instant invention is directed to a method for (i) preventing the onset and progression of schizophrenia and/or (ii) improving symptoms in schizophrenia, which comprises administering a therapeutically effective amount of lurasidone or a pharmaceutically acceptable acid addition salt thereof, and a therapeutically effective amount of a mGluR2 ligand to a mammal in need thereof. The symptoms in schizophrenia include positive symptoms in schizophrenia, negative symptoms in schizophrenia, and cognitive impairment associated with schizophrenia.

Accordingly, one embodiment of the invention is directed to a method for improving (i) positive symptoms in schizophrenia, (ii) negative symptoms in schizophrenia, and/or (iii) cognitive impairment associated with schizophrenia, which comprises administering a therapeutically effective amount of lurasidone or a pharmaceutically acceptable acid addition salt thereof, and a therapeutically effective amount of a mGluR2 ligand to a mammal in need thereof.

One embodiment of the invention is directed to a pharmaceutical product for treating schizophrenia and/or bipolar disorder which comprises a therapeutically effective amount of lurasidone or a pharmaceutically acceptable acid addition salt thereof, and a therapeutically effective amount of a mGluR2 ligand.

One embodiment of the invention is directed to a kit for treating schizophrenia and/or bipolar disorder which comprises a first composition including lurasidone or a pharmaceutically acceptable acid addition salt thereof, and a second composition including a mGluR2 ligand.

One embodiment of the invention is directed to use of a combination comprising lurasidone or a pharmaceutically acceptable acid addition salt thereof, and a mGluR2 ligand in the manufacture of a pharmaceutical composition for treating schizophrenia and/or bipolar disorder.

One embodiment of the invention is directed to use of lurasidone or a pharmaceutically acceptable acid addition salt thereof in the manufacture of a medicament for treating schizophrenia and/or bipolar disorder in combination with a mGluR2 ligand.

One embodiment of the invention is directed to use of lurasidone or a pharmaceutically acceptable acid addition salt thereof in the manufacture of a pharmaceutical composition for potentiating the efficacy of a mGluR2 ligand for treating schizophrenia and/or bipolar disorder.

In addition, one embodiment of the invention is directed to use of a mGluR2 ligand in the manufacture of a pharmaceutical composition for potentiating the efficacy of lurasidone or a pharmaceutically acceptable acid addition salt thereof for treating schizophrenia and/or bipolar disorder.

One embodiment of the invention is directed to a medicament for treating schizophrenia and/or bipolar disorder which comprises lurasidone or a pharmaceutically acceptable acid addition salt thereof, and a mGluR2 ligand.

One embodiment of the invention is directed to a medicament for treating schizophrenia and/or bipolar disorder which comprises lurasidone or a pharmaceutically acceptable acid addition salt thereof for the administration in combination with a mGluR2 ligand.

One embodiment of the invention is directed to a medicament for potentiating the efficacy of a mGluR2 ligand for treating schizophrenia and/or bipolar disorder which comprises lurasidone or a pharmaceutically acceptable acid addition salt thereof.

In addition, one embodiment of the invention is directed to a medicament for potentiating the efficacy of lurasidone or a pharmaceutically acceptable acid addition salt thereof for treating schizophrenia and/or bipolar disorder which comprises a mGluR2 ligand.

In one preferable embodiment, the mGluR2 ligand used herein is a mGluR2 agonist, or a mGluR2 positive allosteric modulator (a mGluR2 PAM).

In one preferable embodiment, the mGluR2 ligand used herein, but is not limited to, is selected from the compounds listed in the following table and pharmaceutically acceptable salts thereof. In more preferable embodiment, the mGluR2 ligand used herein is selected from the group consisting of LY404039, LY2140023, LY379268, LY354740 (eglumetad), LY354740 monohydrate, TS-032, AZD-8529, ADX71149, MGS-0008, MGS-0028, MGS-0039, MGS-0210, BINA, LY487379, and pharmaceutically acceptable salts thereof. In especially preferable embodiment, the mGluR2 ligand used herein is selected from the group consisting of LY379268, LY2140023, LY404039, LY354740 (eglumetad), and pharmaceutically acceptable salts thereof.

| Drug Name [CAS Reg. No.] | Compound Name (Structure) | Reference |
|---|---|---|
| LY404039 [635318-11-5, 191471-54-2] | (−)-(1R,4S,5S,6S)-4-Amino-2-thiabicyclo[3.1.0]hexane-4,6-dicarboxylic acid S,S-dioxide | WO 1997/018199 U.S. Pat. No. 5,688,826 |
| LY2140023 (a prodrug of LY404039) [635318-55-7] | (1R,4S,5S,6S)-4-([(2S)-2-amino-4-(methylthio)-1-oxo-butyl]amino)-2-thiabicyclo-[3.1.0]hexane-4,6-dicarboxylic acid S,S-dioxide | WO 2003/104217 |
| LY379268 [191471-52-0, 191471-50-8 (stereoisomer), 191471-51-9 (stereoisomer)] | (1R,4R,5S,6R)-4-Amino-2-oxabicyclo[3.1.0]hexane-4,6-dicarboxylic acid | WO 1998/032436 U.S. Pat. No. 5,688,826 |
| LY354740 (eglumetad) [176199-48-7] | (+)-(1S,2S,5R,6S)-2-Amino-bicyclo[3.1.0]hexane-2,6-dicarboxylic acid | WO 1997/01526 |

-continued

| Drug Name [CAS Reg. No.] | Compound Name (Structure) | Reference |
|---|---|---|
| LY354740 monohydrate (eglumetad hydrate) [209216-09-1] | (+)-(1S,2S,5R,6S)-2-Amino-bicyclo[3.1.0]hexane-2,6-dicarboxylic acid monohydrate 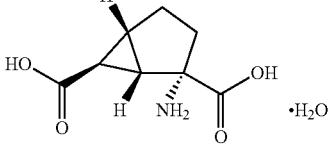 | WO 2000/004010 *Journal of Medicinal Chemistry* (2005), 48(16), 5305-5320 |
| TS-032 (PF-04802540) | 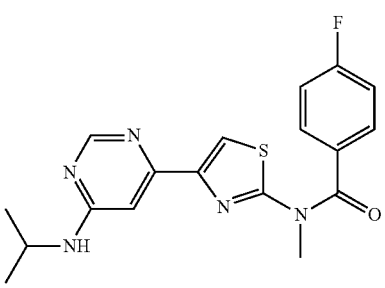 [SMILES: CC(C)Nc1cc(-c2csc(N(C)C(=O)c3ccc(F)cc3)n2)ncn1] | |
| AZD-8529 | 5-[4-[3-[4-(1H-Imidazol-1-yl)phenyl]propyl]piperidin-1-ylmethyl]-7-methyl-2-[4-(trifluoromethoxy)benzyl]-isoindolin-1-one 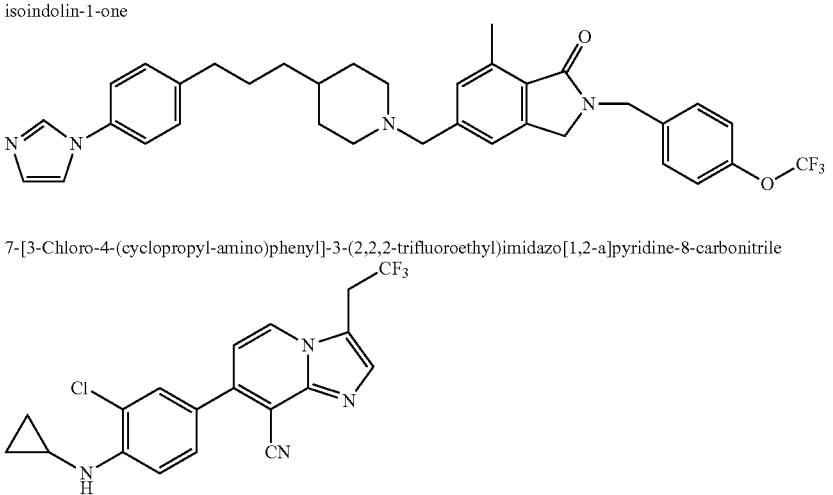 | WO 2006/020879 |
| ADX71149 | 7-[3-Chloro-4-(cyclopropyl-amino)phenyl]-3-(2,2,2-trifluoroethyl)imidazo[1,2-a]pyridine-8-carbonitrile 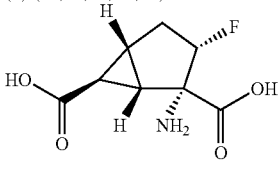 | WO 2009/062676 |
| MGS-0008 [234085-20-2] | (+)-(1S,2S,3S,5R,6S)-2-Amino-3-fluorobicyclo[3.1.0]hexane-2,6-dicarboxylic acid | WO 1999/038839 |
| MGS-0028 [260353-67-1, 321963-33-1] | (1R,2S,5S,6S)-2-Amino-6-fluoro-4-oxobicyclo[3.1.0]-hexane-2,6-dicarboxylic acid 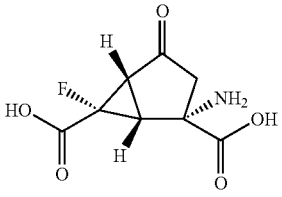 [SMILES: N[C@@]1(C(=O)O)CC(=O)[C@@H]2[C@H]1[C@@]2(F)C(=O)O] | WO 2000/012464 |

| Drug Name [CAS Reg. No.] | Compound Name (Structure) | Reference |
|---|---|---|
| MGS-0039 [569686-87-9] | (1R,2R,3R,5R,6R)-2-Amino-3-(3,4-dichlorobenzyloxy)-6-fluorobicyclo[3.1.0]hexane-2,6-dicarboxylic acid | WO 2003/061698 |
| MGS-0210 (a prodrug of MGS-0039) [820244-38-0] | (1R,2R,3R,5R,6R)-2-Amino-3-(3,4-dichlorobenzyloxy)-6-fluorobicyclo[3.1.0]hexane-2,6-dicarboxylic acid 6-heptyl ester | WO 2005/000791 JP 2006/193507 A |
| BINA (Biphenyl-indanone A) [866823-73-6] | 3'-(2-Cyclopentyl-6,7-dimethyl-1-oxoindan-5-yloxy-methyl)biphenyl-4-carboxylic acid | WO 2006/015158 |
| LY487379 [353231-17-1] | 2,2,2-Trifluoro-N-[4-(2-methoxyphenoxy)phenyl]-N-(pyridin-3-ylmethyl)ethane-sulfonamide | WO 2001/056990 |
| | 3-(4'-Phenoxybiphenyl-4-ylmethyl)-1-oxa-3-azaspiro-[4.5]decan-2-one | WO 2008/032191 |
| | 1-(3-Methylbutyl)-2-oxo-4-(4-phenylpiperidin-1-yl)-1,2-dihydropyridine-3-carbonitrile | WO 2008/107479 |

-continued

| Drug Name [CAS Reg. No.] | Compound Name (Structure) | Reference |
|---|---|---|
| | 2-[4-(4-Chloro-2-fluoro-phenyl)piperidin-1-ylmethyl]-1-methyl-1H-benzimidazole 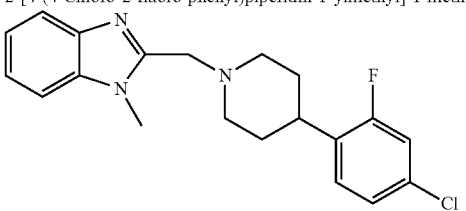 | WO 2008/012623 |
| JNJ-40068782 | 1-(Cyclopropylmethyl)-2-oxo-4-(4-phenylpiperidin-1-yl)-1,2-dihydropyridine-3-carbonitrile 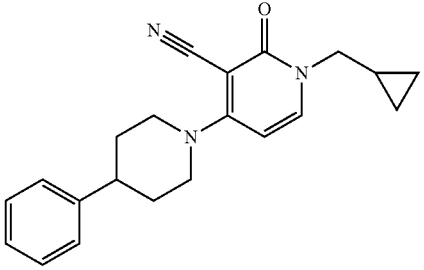 [SMILES: N#Cc1c(N2CCC(c3ccccc3)CC2)ccn(CC2CC2)c1=O] | WO 2008/107479 |
| LY-2607540 | N-[4-[3-Hydroxy-4-isobutyryl-2-(trifluoromethyl)phenoxy-methyl]benzyl]-1-methyl-1H-imidazole-4-carboxamide 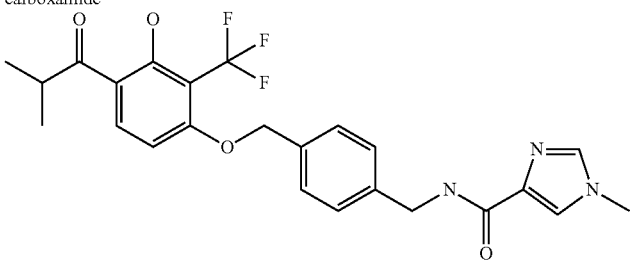 | WO 2010/009062 |
| TBPCOB | 2(S)-(6-tert-Butylpyridin-3-yloxymethyl)-2,3-dihydro-oxazolo[3,2-a]benzimidazole-7-carbonitrile 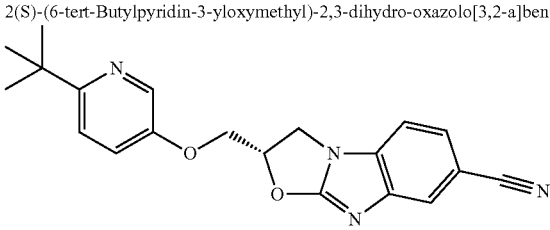 | WO 2009/140163 |

In addition, the mGluR2 ligand used herein also includes the mGluR2 ligands disclosed in the following references.

*Bioorganic & Medicinal Chemistry* (2006), 14(12), 4193-4207.
*Expert Opinion on Therapeutic Patents* (2009) 19(9), 1259-1275.
*Journal of Medicinal Chemistry* 1999 42 (6), 1027-1040 (LY379268, LY389795, LY354740, LY341495, etc.).
*Journal of Medicinal Chemistry* 1999 42 (9), 1546-1555.
*Journal of Medicinal Chemistry* 1999 42 (15), 2816-2827.
*Journal of Medicinal Chemistry* 2000 43 (25), 4893-4909.
*Journal of Medicinal Chemistry* 2002 45 (15), 3171-3183.
*Journal of Medicinal Chemistry* 2005 48 (16), 5305-5320.
*Journal of Medicinal Chemistry* 2007 50 (2), 233-240 (LY389795, LY341495, LY404039, LY404040, etc.).
WO 2010/141360 and WO 2009/110901.

The combination of the present invention is useful for treating schizophrenia and/or bipolar disorder, especially for improving cognitive impairment associated with schizophrenia.

The combination of the present invention may include a combination of lurasidone or a pharmaceutically acceptable acid addition salt thereof, and two or more kinds of mGluR2 ligands.

In the present invention, clozapine may be used instead of lurasidone or together with lurasidone. That is, the combination of the present invention may include a combination of clozapine and a mGluR2 ligand, and a combination of lurasidone, clozapine and a mGluR2 ligand.

The term "mGluR2" is an abbreviation of "metabotropic glutamate receptor 2". The mGluR2 ligand used herein also includes a mGluR2/3 ligand, i.e., a dual ligand acting on both of mGluR2 and mGluR3. Additionally the mGluR2 agonist used herein also includes a mGluR2/3 agonist, and the mGluR2 positive allosteric modulator used herein also includes a mGluR2/3 positive allosteric modulator.

The mGluR2 (mGluR2/3) positive allosteric modulator used herein binds to a site distinct from the glutamate binding site to increase the responses of mGluR2 (mGluR2/3) to glutamate without activating mGluR2 (mGluR2/3) directly.

The method of the instant invention comprising the combined administration can bring in some unexpected effects in the treatment of schizophrenia and/or bipolar disorder. The merits of the instant invention comprising the combined administration include potentiating the efficacy produced by the single-treatment with each medicament, and/or reducing side effects caused by the single-treatment with each medicament. The efficacy includes, for example, but is not limited to, improving "positive symptoms" (hallucinations, delusions, and conceptual disorganization), "negative symptoms" (apathy, social withdrawal, affect, and poverty of speech), and/or "cognitive impairment" (confused thinking and speech or disorganized behavior and perception) of schizophrenia. The side effects include, for example, but are not limited to, extrapyramidal or CNS depressant side effects.

BEST MODE FOR CARRYING OUT THE INVENTION

Figure 1:
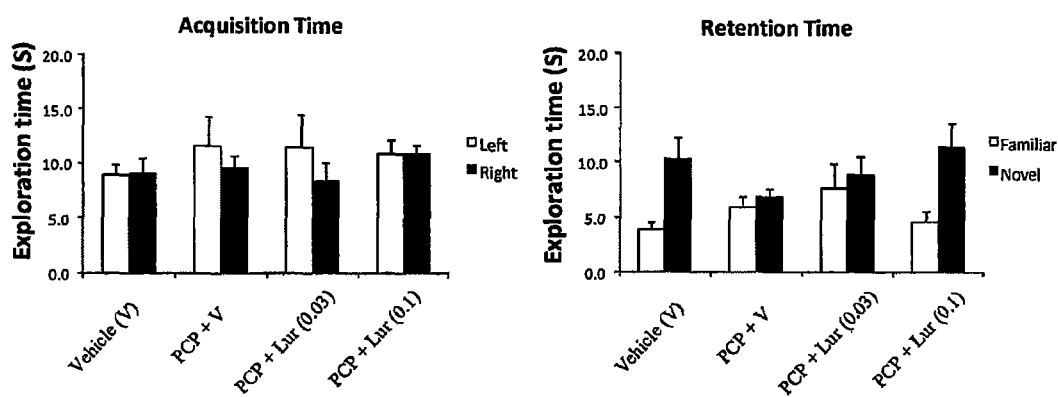
FIG. 1 shows the effect of acute administration of lurasidone HCl (0.03 mg/kg and 0.1 mg/kg), after subchronic PCP treatment.

Lurasidone may be used in form of the free base, optionally in form of its pharmaceutically acceptable acid addition salt and/or optionally in form of the hydrate and/or solvate thereof. Suitable acid addition salts include, for example, those of the acids selected from succinic acid, hydrobromic acid, acetic acid, fumaric acid, maleic acid, methanesulphonic acid, lactic acid, phosphoric acid, hydrochloric acid, sulphuric acid, tartaric acid and citric acid. Mixtures of the above-mentioned acid addition salts may also be used. From the aforementioned acid addition salts the hydrochloride and the hydrobromide, particularly the hydrochloride, are preferred.

The mGluR2 ligand used herein may also be capable of forming its acid addition salt with a pharmaceutically acceptable acid. Representative salts include the following: acetate, benzenesulfonate, benzoate, bicarbonate, bisulfate, bitartrate, borate, hydrobromide, camsylate, carbonate, hydrochloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, hydroiodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Furthermore, where the mGluR2 ligand used herein carries an acidic moiety, a suitable pharmaceutically acceptable salt thereof may include alkali metal salt, e.g., sodium or potassium salt; alkaline earth metal salt, e.g., calcium or magnesium salt; and salt formed with suitable organic ligand, e.g., quaternary ammonium salt.

The mGluR2 ligand used herein may have chiral centers and occur as racemate, racemic mixture and as individual diastereomer, or enantiomer with all isomeric forms being included in the present invention. Therefore, where a compound is chiral, the separate enantiomers, substantially free of the other, are included within the scope of the invention. Further included are all mixtures of the two enantiomers. Also included within the scope of the invention are polymorphs and hydrates of the mGluR2 ligand of the instant invention.

The present invention includes within its scope prodrugs of lurasidone and the mGluR2 ligand. In general, such prodrugs will be functional derivatives of the compounds of this invention which are readily convertible in vivo into the required compound.

The exemplified prodrugs of the invention, but are not limited to, include the following types:

Ester prodrug for carboxyl, hydroxyl or thiol group of the parent drug.

Phosphate ester prodrug for hydroxyl or amine group of the parent drug.

Carbonate or carbamate prodrug for carboxyl, hydroxyl or amine group of the parent drug.

Amide prodrug for carboxylic acid or amine group of the parent drug.

Amino acid-attached prodrug for carboxylic acid or amine group of the parent drug.

Oxime prodrug for ketone, amidine or guanidine group of the parent drug.

The prodrugs of the invention can be prepared, for example, by means disclosed in *Nature Reviews Drug Discovery* 7; 255-270 (2008); or *Journal of Medicinal Chemistry* 2005, 48 (16), 5305-5320.

The term "therapeutically effective amount" shall mean the amount of a drug or pharmaceutical agent that will elicit the biological or medical response of a tissue, system, animal or human that is being sought by a researcher or clinician.

The terms "treating" and "treatment" used herein include any treatment of the disease (e.g. improvement of the symptoms, relief of the symptoms, arrest of the development of the symptoms, etc.) as well as any prevention of the disease (e.g. prevention of the onset and/or progression of the disease).

As used herein, the term "pharmaceutical product" is intended to encompass a product comprising the specified ingredients in the specified amounts, as well as any product which results, directly or indirectly, from combination of the specified ingredients in the specified amounts.

As used herein, the term "schizophrenia" includes, but is not limited to, the disorganized type, the catatonic type, the paranoid type, the undifferentiated type, the residual type of schizophrenia, schizoaffective disorder, schizophreniform disorder, delusional disorder, brief psychotic disorder, shared psychotic disorder, psychotic disorder due to a general medical condition, substance-induced psychotic disorder, and psychotic disorder not otherwise specified. In addition, the symptoms of schizophrenia include positive symptoms in schizophrenia, negative symptoms in schizophrenia, and cognitive impairment associated with schizophrenia.

As used herein, the term "bipolar disorder" includes, but is not limited to, bipolar I, bipolar II, cyclothymia and other types based on the nature and severity of mood episodes experienced.

In the combination of the present invention, lurasidone and the mGluR2 ligand may be administered separately or together in one pharmaceutical composition. In addition, the administration of one element of the combination of the present invention may be prior to, concurrent with, or subsequent to the administration of the other element of the combination.

The elements of the combination of two active ingredients of the invention (lurasidone and the mGluR2 ligand) may be administered by oral, parenteral (e.g., intramuscular, intraperitoneal, intravenous or subcutaneous injection, or implant), buccal, nasal, vaginal, rectal, sublingual, or topical (e.g., ocular eyedrop) routes of administration and may be formulated alone or together, in suitable dosage unit formulations containing conventional non-toxic pharmaceutically acceptable carriers, adjuvants and vehicles appropriate for each route of administration.

The pharmaceutical product for the administration of the two active ingredients of the invention may conveniently be presented in dosage unit form and may be prepared by any of the methods well known in the art of pharmacy. All methods include the step of bringing the active ingredients into association with a carrier which is constituted of one or more accessory ingredients. In general, the pharmaceutical product is prepared by uniformly and intimately bringing the active ingredients into association with a liquid carrier or a finely divided solid carrier or both, and then, if necessary, shaping the product into the desired dosage form. In the pharmaceutical compositions the active compounds are included in an amount sufficient to produce the desired pharmacologic effect.

The pharmaceutical product containing the two active ingredients, separately or together, that are suitable for oral administration may be in the form of discrete units such as hard or soft capsules, tablets, troches or lozenges, each containing a predetermined amount of the active ingredients, in the form of a dispersible powder or granules, and so on.

Dosage forms intended for oral use may be prepared according to any method known to the art for the manufacture of pharmaceutical formulations and such compositions. The excipients used orally may be, for example, inert diluents, granulating and disintegrating agents, binding agents, and lubricating agents.

The dosage of the active ingredients in the compositions of this invention may be varied. However, it is necessary that the amount of the two active ingredients can be such that a suitable dosage form is obtained. The selected dosage and the dosage form depend upon the desired therapeutic effect, on the route of administration and on the duration of the treatment. Dosage ranges in the combination are approximately 0.3 to 1.0 time, preferably 0.5 to 1.0 time the clinically effective ranges required to induce the desired therapeutic effect, respectively when the compounds are used singly.

A daily dosage of each medicament for adults includes the following dosages, for example. In the following list, for example, "400 mg t.i.d." means that 400 mg which is a daily dosage is administered in 3 portions.

Lurasidone HCl: 1-400 mg q.d., preferably 10-200 mg q.d., more preferably 20-160 mg q.d.

Lurasidone (free form) or a pharmaceutically acceptable acid addition salt of Lurasidone: the equivalent dose of the above Lurasidone HCl (i.e., the lurasidone molarity of which corresponds to that of the above Lurasidone HCl).

Clozapine: 1-900 mg q.d. or b.i.d., preferably 12.5-900 mg q.d. or b.i.d., more preferably 12.5-450 mg/kg q.d. or b.i.d.

LY2140023: 1-400 mg q.d., b.i.d, or t.i.d., preferably 10-400 mg q.d., b.i.d., or t.i.d., more preferably 20-200 mg q.d., b.i.d., or t.i.d.

LY404039: 1-4000 mg q.d., b.i.d., or t.i.d., preferably 10-4000 mg q.d., b.i.d., or t.i.d., more preferably 20-2000 mg q.d., b.i.d., or t.i.d. (recommended single treatment doses in rodent models: 3-30 mg/kg, i.p).

LY379268: 1-400 mg q.d., b.i.d., or t.i.d., preferably 10-400 mg q.d., b.i.d., or t.i.d., more preferably 20-200 mg q.d., b.i.d., or t.i.d. (recommended single treatment doses in rodent models: 0.3-3 mg/kg, i.p.).

LY354740: 1-400 mg q.d., b.i.d, or t.i.d.

AZD-8529: 1-400 mg q.d., b.i.d, or t.i.d., preferably 10-400 mg q.d., b.i.d., or t.i.d., more preferably 20-200 mg q.d., b.i.d., or t.i.d.

ADX-71149: 0.1-1000 mg q.d., b.i.d or t.i.d.

TS-032: 0.1-1000 mg q.d., b.i.d, or t.i.d.

JNJ-40068782: 1-400 mg q.d., b.i.d, or t.i.d.

LY-2607540: 1-400 mg q.d., b.i.d, or t.i.d.

TBPCOB: 1-400 mg q.d., b.i.d, or t.i.d.

Other mGluR2 ligands listed in Paragraph [0016]: 1-400 mg q.d., b.i.d, t.i.d.

When the two active ingredients are prepared in a single dosage form, they are incorporated in a ratio of 0.1 to 100 parts by weight, preferably 0.2 to 50 parts by weight of mGluR2 ligand per 1 part by weight of lurasidone, lurasidone HCl or a pharmaceutically acceptable acid addition salt thereof. And, the drug combination may include the sum of the ingredients in 0.1-70% (w/w) per the preparation, but not limited thereto.

EXAMPLE 1

Experimental Procedure

Female Long-Evans rats received vehicle or PCP (2 mg/kg, i.p.) twice daily for 7 days, followed by a 7-day washout period (n=6-9/group). Phencyclidine (PCP) which is known to induce schizophrenia-like symptoms in human normal subjects and to exacerbate symptoms in patients with schizophrenia was dissolved in distilled water and administered in a volume of 1 ml/kg.

On the test day, in the first set of experiments, lurasidone HCl (0.03 and 0.1 mg/kg; produced by Dainippon Sumitomo Pharma Co., Ltd.), clozapine (0.3 mg/kg), LY379268 (1 mg/kg; Tocris Bioscience) alone, or haloperidol (0.1 mg/kg), pimavanserin (3 mg/kg), lurasidone HCl (0.03 mg/kg), clozapine (0.1 mg/kg) in combination with LY379268 (1 mg/kg) were administered intraperitoneally in a volume of 1 ml/kg, 30 min before the novel object recognition (NOR) test. In the second set of experiments, LY404039 (1 mg/kg; produced by Dainippon Sumitomo Pharma Co., Ltd.) alone was orally administered in a volume of 4 ml/kg 60 min before the novel object recognition (NOR) test. For combination with lurasidone HCl, LY404039 (1 mg/kg, p.o.) and lurasidone HCl (0.03 mg/kg, i.p.) were administered 60 min and 30 min before the novel object recognition (NOR) test, respectively.

In the third set of experiments, BINA (30 mg/kg; produced by Dainippon Sumitomo Pharma Co., Ltd.) alone or BINA (30 mg/kg) in combination with lurasidone HCl (0.03 mg/kg) was administered intraperitoneally in a volume of 1 ml/kg 30 min before the novel object recognition (NOR) test.

Haloperidol, pimavanserin, and LY404039 were dissolved in distilled water. Lurasidone HCl was dissolved 0.5% methylcellulose, 0.2% Tween 80. Clozapine was dissolved in a small amount of 0.1 M phosphoric acid, and the pH was adjusted to 6 to 7 with 0.1 N NaOH. LY379268 was dissolved in saline. BINA was dissolved in 10% Tween 80, 10% 1N NaOH, and the pH was adjusted to 7 with 1N HCl.

Novel Object Recognition (NOR) Test

Apparatus.

The object recognition test was performed in an open field comprising a square box made of Plexiglas (52/52/31 cm) placed 37 cm above the floor on an immoveable stand. The floor of the box was white with black gridlines forming nine identical squares on it. All other walls were black. A video camera connected to a video recorder and monitor was positioned above the box. The objects used for the test consisting of four heavy pyramidal structures made of metal or Perspex that could not be displaced by the animals. Care was taken to ensure that these objects were not of any natural significance to the rats.

Object Recognition Testing.

Testing was carried out according to a previously validated method (Grayson et al., Behav. Brain Res. 2007 184, 31-38; Snigdha et al., J. Pharmacol. Exp. Ther., 2010 332 (2), 622-31). The rats were familiarized to the test environment and NOR arena before the test day. Habituation consisting of placing the subjects in the empty NOR arena for 1 h, on the day before the test day (day 1). Before behavioral testing on day 2, rats were given a further 3-min habituation. For each experimental trial after the 3-min habituation period, the rats were given two 3-min trials (T1 and T2), separated by a 1-min intertrial interval in the home cage during which the objects were changed and the arena was cleaned. In Trial 1 (T1) or the acquisition trial, the animals were allowed to explore two identical objects (A1 and A2) for 3 min. In the second trial (T2) or the retention trial, the animals explored a familiar object (A) from T1 and a novel object (B) for 3 min. The familiar object presented during T2 was a duplicate of the object presented in T1 to avoid any olfactory trails. Each rat was tested three or four times in the NOR paradigm. To reduce carryover effects, a 7-day washout period was given between each of the test sessions. The criterion for continuing to test the rats was based on mean total exploration time in the acquisition or retention phase 5 seconds. If a rat did not explore at least that amount, they were excluded from the analysis. This happened rarely and not enough to affect the ability to use the remaining animals for analysis.

Data Collection.

Behavior in all trials was recorded on video for subsequent blind scoring for the following parameters: total exploration time of both objects in the acquisition trial(s), total exploration time of objects in the retention trial(s). Object exploration is defined by animals licking, sniffing, or touching the object with the forepaws while sniffing, but not leaning against, turning around, standing, or sitting on the object. The exploration time(s) of each object in each trial was recorded by use of two stopwatches.

Result 1

The effect of acute administration of lurasidone HCl (0.03 mg/kg and 0.1 mg/kg), after subchronic PCP treatment. Data are shown in the following table as mean±SEM of exploration time. n=7 to 8 rats per group.

The summarized result is shown in FIG. 1. Subchronic PCP treatment had no significant effect on object exploration in the acquisition trial. In the retention trial, vehicle-treated rats had a clear preference for novel compared to familiar objects. This effect was abolished in sub-chronic PCP treated rats which explored both objects for an equal amount of time. Acute treatment with lurasidone HCl reversed the PCP-induced NOR deficits and the effective dose was 0.1 mg/kg.

|  | Acquisition (sec) | | Retention (sec) | |
| --- | --- | --- | --- | --- |
|  | Left | Right | Familiar | Novel |
| Vehicle | 8.9 ± 1.0 | 9.0 ± 1.4 | 3.9 ± 0.6 | 10.3 ± 2.1 |
| PCP + Vehicle | 11.5 ± 2.7 | 9.5 ± 1.2 | 5.9 ± 0.9 | 6.8 ± 0.8 |
| PCP + Lurasidone HCl (0.03 mg/kg) | 11.4 ± 3.1 | 8.3 ± 1.8 | 7.6 ± 2.3 | 8.9 ± 1.7 |
| PCP + Lurasidone HCl (0.1 mg/kg) | 10.9 ± 1.3 | 10.9 ± 0.8 | 4.6 ± 1.0 | 11.4 ± 2.2 |

Result 2

The effect of acute administration of LY379268 (1 mg/kg), LY379268 (1 mg/kg) plus lurasidone HCl (0.03 mg/kg, sub-effective dose), and LY379268 (1 mg/kg) plus pimavanserin (3 mg/kg) after subchronic PCP treatment. Data are shown in the following table as mean±SEM of exploration time. n=6 to 8 rats per group.

Figure 2:
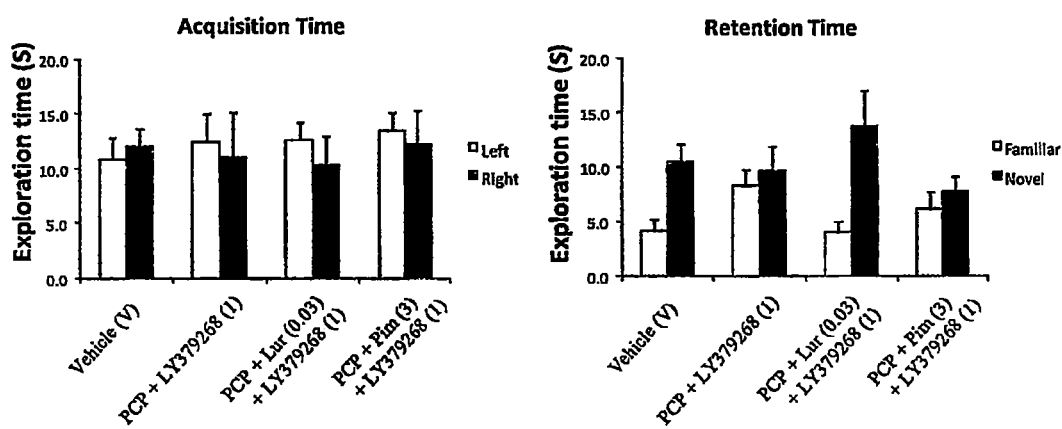
FIG. 2 shows the effect of acute administration of LY379268 (1 mg/kg), LY379268 (1 mg/kg) plus lurasidone HCl (0.03 mg/kg, sub-effective dose), and LY379268 (1 mg/kg) plus pimavanserin (3 mg/kg) after subchronic PCP treatment.

The summarized result is shown in FIG. 2. LY379268 alone did not attenuate the PCP-induced NOR deficits. However, co-administration of LY379268 with sub-effective dose of lurasidone HCl but with pimavanserin significantly reversed the PCP-induced deficits.

|  | Acquisition (sec) | | Retention (sec) | |
| --- | --- | --- | --- | --- |
|  | Left | Right | Familiar | Novel |
| Vehicle | 10.9 ± 2.0 | 12.0 ± 1.6 | 4.1 ± 1.1 | 10.5 ± 1.7 |
| PCP + LY379268 (1 mg/kg) | 12.4 ± 2.6 | 11.0 ± 4.2 | 8.3 ± 1.5 | 9.7 ± 2.2 |
| PCP + Lurasidone HCl (0.03 mg/kg) + LY379268 (1 mg/kg) | 12.7 ± 1.6 | 10.3 ± 2.6 | 4.0 ± 1.0 | 13.8 ± 3.2 |
| PCP + Pimavanserin (3 mg/kg) + LY379268 (1 mg/kg) | 13.5 ± 1.6 | 12.3 ± 3.1 | 6.1 ± 1.6 | 7.8 ± 1.4 |

Result 3

The effect of acute administration of LY379268 (1 mg/kg) plus haloperidol (0.1 mg/kg), and clozapine (0.1, 0.3 mg/kg) after subchronic PCP treatment. Data are shown in the following table as mean±SEM of exploration time. n=6 to 8 rats per group.

Figure 3:
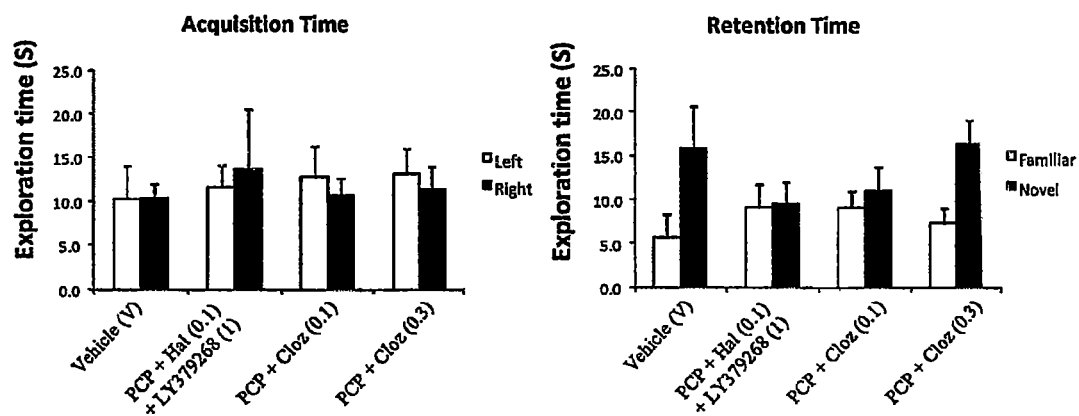
FIG. 3 shows the effect of acute administration of LY379268 (1 mg/kg) plus haloperidol (0.1 mg/kg), and clozapine (0.1, 0.3 mg/kg) after subchronic PCP treatment.

The summarized result is shown in FIG. 3. Co-administration of LY379268 with haloperidol did not reverse the NOR deficits induced by PCP. Clozapine reversed the PCP-induced NOR deficits and the effective dose was 0.3 mg/kg.

|  | Acquisition (sec) | | Retention (sec) | |
| --- | --- | --- | --- | --- |
|  | Left | Right | Familiar | Novel |
| Vehicle | 10.3 ± 3.8 | 10.4 ± 1.6 | 5.6 ± 2.6 | 15.9 ± 4.8 |
| PCP + Haloperidol (0.1 mg/kg) + LY379268 (1 mg/kg) | 11.7 ± 2.4 | 13.7 ± 6.8 | 9.2 ± 2.5 | 9.5 ± 2.5 |
| PCP + Clozapine (0.1 mg/kg) | 12.7 ± 3.5 | 10.6 ± 2.1 | 9.1 ± 1.9 | 11.0 ± 2.8 |
| PCP + Clozapine (0.3 mg/kg) | 13.1 ± 2.9 | 11.4 ± 2.5 | 7.3 ± 1.7 | 16.3 ± 2.8 |

Result 4

The effect of acute administration of LY379268 (1 mg/kg) plus clozapine (0.1 mg/kg, sub-effective dose) after sub-chronic PCP treatment. Data are shown in the following table as mean±SEM of exploration time. n=8 to 9 rats per group.

Figure 4:
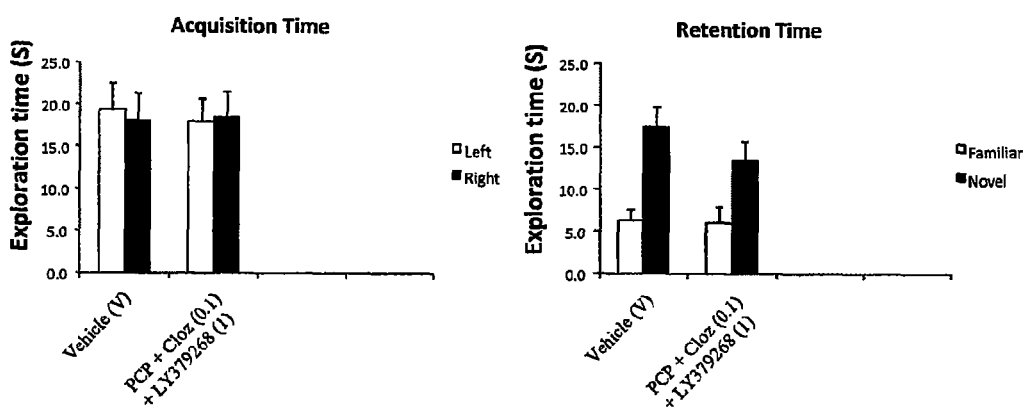
FIG. 4 shows the effect of acute administration of LY379268 (1 mg/kg) plus clozapine (0.1 mg/kg, sub-effective dose) after subchronic PCP treatment.

The summarized result is shown in FIG. 4. Co-administration of LY379268 with sub-effective dose of clozapine significantly reversed the PCP-induced deficits.

|  | Acquisition (sec) | | Retention (sec) | |
| --- | --- | --- | --- | --- |
|  | Left | Right | Familiar | Novel |
| Vehicle | 19.3 ± 3.1 | 18.1 ± 3.2 | 6.3 ± 1.4 | 17.3 ± 2.4 |
| PCP + Clozapine (0.1 mg/kg) + LY379268 (1 mg/kg) | 18.0 ± 2.7 | 18.5 ± 3.1 | 6.1 ± 1.7 | 13.4 ± 2.4 |

Result 5

The effect of acute administration of LY404039 (1 mg/kg) and LY404039 (1 mg/kg) plus lurasidone HCl (0.03 mg/kg, sub-effective dose) after subchronic PCP treatment. Data are shown in the following table as mean±SEM of exploration time. n=7 to 8 rats per group.

Figure 5:
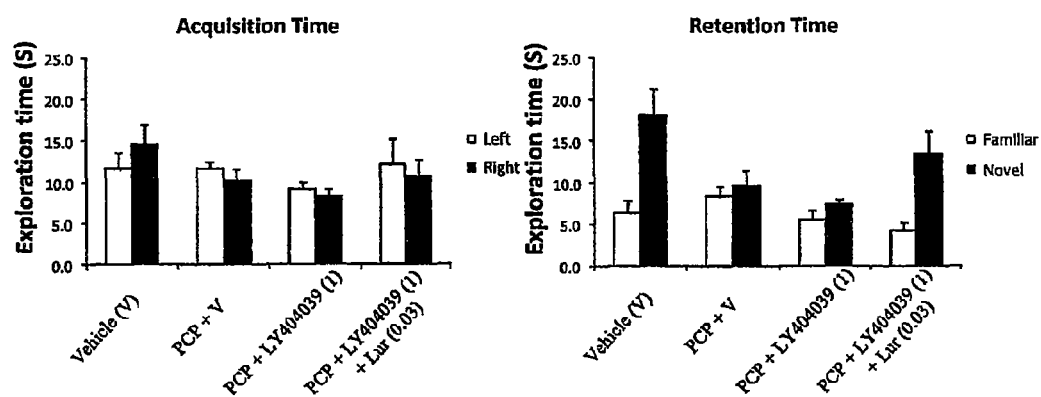
FIG. 5 shows the effect of acute administration of LY404039 (1 mg/kg) and LY404039 (1 mg/kg) plus lurasidone HCl (0.03 mg/kg, sub-effective dose) after subchronic PCP treatment.

The summarized result is shown in FIG. 5. LY404039 alone did not attenuate the PCP-induced NOR deficits. However, co-administration of LY404039 with sub-effective dose of lurasidone HCl significantly reversed the PCP-induced deficits.

|  | Acquisition (sec) | | Retention (sec) | |
| --- | --- | --- | --- | --- |
|  | Left | Right | Familiar | Novel |
| Vehicle | 11.7 ± 1.9 | 14.7 ± 2.3 | 6.3 ± 1.6 | 18.0 ± 3.2 |
| PCP + Vehicle | 11.7 ± 0.8 | 10.3 ± 1.3 | 8.3 ± 1.3 | 9.6 ± 2.0 |
| PCP + LY404039 (1 mg/kg) | 9.3 ± 0.8 | 8.4 ± 0.9 | 5.5 ± 1.1 | 7.3 ± 0.8 |
| PCP + Lurasidone HCl (0.03 mg/kg) + LY404039 (1 mg/kg) | 12.3 ± 2.9 | 10.8 ± 2.1 | 4.3 ± 0.9 | 13.5 ± 2.7 |

Result 6

The effect of acute administration of BINA (30 mg/kg) and BINA (30 mg/kg) plus lurasidone HCl (0.03 mg/kg, sub-effective dose) after subchronic PCP treatment. Data are shown in the following table as mean±SEM of exploration time. n=7 to 9 rats per group.

Figure 6:
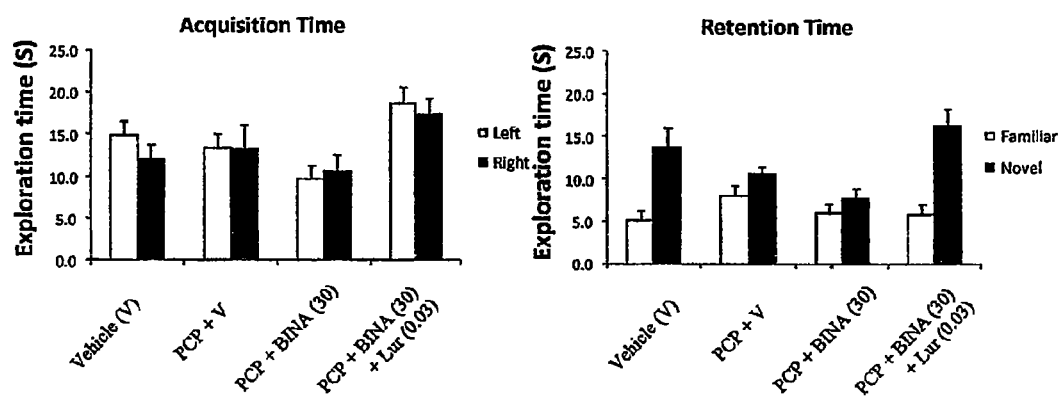
FIG. 6 shows the effect of acute administration of BINA (30 mg/kg) and BINA (30 mg/kg) plus lurasidone HCl (0.03 mg/kg, sub-effective dose) after subchronic PCP treatment.

The summarized result is shown in FIG. 6. BINA alone did not attenuate the PCP-induced NOR deficits. However, co-administration of BINA with sub-effective dose of lurasidone HCl significantly reversed the PCP-induced deficits.

|  | Acquisition (sec) | | Retention (sec) | |
| --- | --- | --- | --- | --- |
|  | Left | Right | Familiar | Novel |
| Vehicle | 14.9 ± 1.7 | 12.0 ± 1.8 | 5.1 ± 1.1 | 13.8 ± 2.3 |
| PCP + Vehicle | 13.4 ± 1.7 | 13.3 ± 2.9 | 8.1 ± 1.2 | 10.7 ± 0.7 |
| PCP + BINA (30 mg/kg) | 9.8 ± 1.5 | 10.7 ± 2.0 | 6.0 ± 1.1 | 7.9 ± 1.0 |
| PCP + Lurasidone HCl (0.03 mg/kg) + BINA (30 mg/kg) | 18.8 ± 1.9 | 17.4 ± 1.9 | 5.9 ± 1.2 | 16.4 ± 2.0 |

These results indicate that mGluR2/3 agonism is relevant to the ability of atypical APDs (antipsychotic drugs) to ameliorate the effect of sub-chronic PCP, a putative measure of cognitive impairment associated with schizophrenia. This suggests combined administration of mGluR2/3 agonists with at least some atypical APDs may be a way to minimize side effects from the atypical APDs and possibly enhance efficacy for cognition and other domains of psychopathology.

The same experiment as mentioned above is carried out using any one of the medicaments listed in Paragraph [0016] or a salt thereof, instead of LY379268. According to the experiment, the combined effect of lurasidone and each medicament can be evaluated in the improvement of cognitive impairment associated with schizophrenia.

EXAMPLE 2

Using the following method, the combined effect of lurasidone and LY404039 can be evaluated in the improvement of positive symptoms in schizophrenia.

Effect of lurasidone adjunctive with mGluR2/3 agonist LY404039 is examined in an animal model with phencyclidine (PCP) for predicting antipsychotic activity. Male C57BL/6J mice at age of 8 weeks (n=8 per group) are used for experiment. Lurasidone HCl (0.3-10 mg/kg, p.o., 10 mL/kg in 0.5% methylcellulose) and LY404039 (0.3-10 mg/kg, i.p., 10 mL/kg in saline) are administered 60 min and 30 min prior to administration of PCP (4.5 mg/kg, s.c., 10 mL/kg in saline), respectively. Subsequently, spontaneous locomotor activity of each mouse is automatically measured with SCANET (MV-20 plus, Melquest Co., Ltd.) for 55 min. Total activities for 55 min are statistically compared among groups.

EXAMPLE 3

The same experiment as EXAMPLE 2 is carried out using any one of the medicaments listed in Paragraph [0016] or a salt thereof, instead of LY404039. According to the experiment, the combined effect of lurasidone and each medicament can be evaluated in the improvement of positive symptoms in schizophrenia.

EXAMPLE 4

Using the following method, the combined effect of lurasidone and LY404039 can be evaluated in the treatment of bipolar disorder (K. Okada et al., *Pharmacol Biochem Behav.* 35(4): 897-901 (1990)).

Effect of lurasidone adjunctive with mGluR2/3 agonist LY404039 is examined in an animal model with methamphetamine and chlordiazepoxide mixture for predicting antimanic activity. Male C57BL/6J mice (n=8 per group, 20-26 g body weight) are used for experiment. Lurasidone HCl (0.3-10 mg/kg, p.o., 10 mL/kg in 0.5% methylcellulose) is administered 30 min prior to administration of LY404039 (0.3-10 mg/kg, i.p., 10 mL/kg in saline) in combination with methamphetamine (4 mg/kg, i.p., 10 mL/kg in saline) and chlordiazepoxide (10 mg/kg, i.p., 10 mL/kg in saline). Subsequently, digital image for freely moving mouse in acrylic cage (W 360 mm×D 230 mm×H 310 mm) is recorded for 90 min and travel distance for 60 min after initial 30 min habituation period is automatically measured with Noldus Ethovision software ver 3.1. Travel distances are statistically compared among groups.

EXAMPLE 5

The same experiment as EXAMPLE 4 is carried out using any one of the medicaments listed in Paragraph [0016] or a salt thereof, instead of LY404039. According to the experiment, the combined effect of lurasidone and each medicament can be evaluated in the treatment of bipolar disorder.

EXAMPLE 6

Using the following method with NOR test as shown in EXAMPLE 1, the combined effect of lurasidone HCl and LY379268 can be evaluated in the treatment to prevent the onset and progression of schizophrenia. LY379268 (1 mg/kg) and lurasidone HCl (0.03 mg/kg) are co-administered intraperitoneally in a volume of 1 mL/kg to female Long-Evans rats (n=6-9/group) 30 min before every treatment with PCP (2 mg/kg, twice a day, i.p.) for 7 days (day 1-7). Subsequently, rats are given a 7-days drug-free period prior to NOR testing (day 8-14). On day 15, the NOR test is performed.

EXAMPLE 7

The same experiment as EXAMPLE 6 is carried out using any one of the medicaments listed in Paragraph [0016] or a salt thereof, instead of LY379268. According to the experiment, the combined effect of lurasidone and each medicament can be evaluated in the treatment to prevent the onset and progression of schizophrenia.

EXAMPLE 8

Using the following method, the combined effect of lurasidone HCl and LY404039 can be evaluated in the improvement of negative symptoms in schizophrenia. PCP (10 mg/kg, s.c.) was administered to male ICR mice (6 weeks of age, n=8/group) twice a day for 5 days. Two to five days later, the social interaction test was carried out according to a previously validated method (D. Wang, et al., Neuropharmacology 2007, 52, 1179-1187). After mice were placed in a acrylic square arena (30×45×40 cm) for 3 hrs under light, each mouse was separated and habituated to the arena under dark condition for 15 min. Then every mouse was randomly assigned to an unfamiliar partner in each drug-treated group. Immediately after partnering in the arena, the behavior was recorded by a video camera for min, and the time that a pair spent in social interaction (sniffing and grooming the partner, following, mounting, and crawling under or over the partner) was recorded by an observer who was blind to the drug treatment. LY379268 (1 mg/kg) and lurasidone HCl (0.03 mg/kg) are co-administered intraperitoneally in a volume of 1 mL/kg to mice 30 min before partnering.

EXAMPLE 9

The same experiment as EXAMPLE 8 is carried out using any one of the medicaments listed in Paragraph [0016] or a salt thereof, instead of LY404039. According to the experiment, the combined effect of lurasidone and each medicament can be evaluated in the improvement of negative symptoms in schizophrenia.

FIG. 1: the sub-effective dose is 0.03 mg/kg and the effective dose is 0.1 mg/kg for a lurasidone dose response curve.

FIG. 2: LY379268 did not attenuate the PCP-induced deficit in NOR. However, co-administration of LY379268 with sub-effective dose of lurasidone, but with Pimavanserin significantly reversed the PCP-induced deficit.

FIG. 3: co-administration of LY379768 with Haloperidol did not reverse the PCP-induced deficit. The sub-effective close Clozapine is 0.1 mg/kg and the effective dose is 0.3 mg/kg in a Clozapine response curve.

FIG. 4: co-administration of LY379268 with a sub-effective dose of Clozapine significantly reduced the PCP-induced deficit.

FIG. 5: LY404039 did not improve the PCP-induced deficit in NOR. However, co-administration of LY 404039 with a sub-effective dose of lurasidone significantly reversed the PCP-induced deficit.

FIG. 6: BINA did not improve the PCP-induced deficit in NOR. However, co-administration of BINA with sub-effective dose of lurasidone significantly reversed the PCP-induced deficit.

The invention claimed is:

1. A method for treating schizophrenia and/or bipolar disorder which comprises administering a therapeutically effective amount of lurasidone or a pharmaceutically acceptable acid addition salt thereof, and a therapeutically effective amount of a mGluR2 ligand to a mammal in need thereof.

2. The method of claim 1 wherein treating schizophrenia and/or bipolar disorder is treating schizophrenia.

3. The method of claim 2 wherein treating schizophrenia is improving (i) positive symptoms in schizophrenia, (ii) negative symptoms in schizophrenia, and/or (iii) cognitive impairment associated with schizophrenia.

4. The method of claim 2 wherein treating schizophrenia is improving cognitive impairment associated with schizophrenia.

5. A method for improving cognitive impairment associated with schizophrenia which comprises administering a therapeutically effective amount of lurasidone or a pharmaceutically acceptable acid addition salt thereof, and a therapeutically effective amount of a mGluR2 ligand to a mammal in need thereof.

6. The method of claim 1 wherein the mGluR2 ligand is a mGluR2 agonist.

7. The method of claim 1 wherein the mGluR2 ligand is a mGluR2 positive allosteric modulator.

8. The method of claim 1 wherein the mGluR2 ligand is one or more selected from the group consisting of LY404039, LY2140023, LY379268, LY354740 (eglumetad), LY354740 monohydrate, TS-032, AZD-8529, ADX71149, MGS-0008, MGS-0028, MGS-0039, MGS-0210, BINA, LY487379, and pharmaceutically acceptable salts thereof.

9. The method of claim 1 wherein the mGluR2 ligand is one or more selected from the group consisting of LY379268, LY2140023, LY404039, LY354740 (eglumetad), and pharmaceutically acceptable salts thereof.

10. The method of claim 1 wherein the mGluR2 ligand is one or more selected from the group consisting of LY379268, LY404039, BINA, and pharmaceutically acceptable salts thereof.

11. The method of claim 1 wherein the mGluR2 ligand is one or more selected from the group consisting of LY404039 and pharmaceutically acceptable salts thereof.

* * * * *